United States Patent [19]

Cassal

[11] Patent Number: 4,680,290
[45] Date of Patent: Jul. 14, 1987

[54] STEROIDS FOR THE TREATMENT OF HYPERCHOLESTEROLEMIA

[75] Inventor: Jean-Marie Cassal, Mulhouse, France

[73] Assignee: Hoffmann-La Roche Inc., Nutley, N.J.

[21] Appl. No.: 639,543

[22] Filed: Aug. 10, 1984

[30] Foreign Application Priority Data

Aug. 25, 1983 [CH] Switzerland .......................... 4644/83

[51] Int. Cl.$^4$ .......................... A61K 31/56; C07J 9/00
[52] U.S. Cl. .................................. 514/182; 260/397.2
[58] Field of Search ...................... 260/397.2; 514/182

[56] References Cited

U.S. PATENT DOCUMENTS 3,248,408 4/1966 Grier et al. ...................... 260/397.45

OTHER PUBLICATIONS

Chemical Abstracts (1979), vol. 91, Par. 34,466(a) relied on.
Ramirez et al., J. Org. Chem., vol. 43, No. 12 (1978), pp. 2331–2334.
Ramirez et al., Int. Journal Methods in Syn. Org. Chem., No. 10 (1977), pp. 673–675.
Chem. Abstracts 91:34466.
Chem. Abstracts 91:57297k.
Chem. Abstracts 92:53745c.
Chem. Abstracts 94:80055a.
Chem. Abstracts 89:23755.

Primary Examiner—Leonard Schenkman
Attorney, Agent, or Firm—Jon S. Saxe; Bernard S. Leon; Matthew Boxer

[57] ABSTRACT

Steroids of the formula

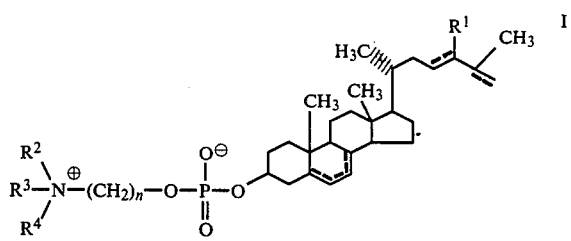

wherein n represents the number 2, 3 or 4; $R^1$ represents hydrogen, lower-alkyl or lower-alkylidene; $R^2$, $R^3$ and $R^4$ represent hydrogen or lower-alkyl and the dotted C—C bonds in the 5(6)-, 7(8)-, 22(23)-, 24(28)- and 25(26)-position are optional, whereby the B-ring can contain only one double bond and the side-chain is either saturated or is mono-unsaturated or is di-unsaturated in the 22(23), 25(26)-position; and whereby $R^1$ is lower-alkyl or lower-alkylidene when a 5(6)-double bond is present, n is 2 and $R^2$, $R^3$ and $R^4$ are methyl, and pharmaceutically acceptable salts of these steroids have activity inhibiting the intestinal resorption of cholesterol. They can be manufactured from steroids which are otherwise substituted in the 3β-position.

24 Claims, No Drawings

STEROIDS FOR THE TREATMENT OF HYPERCHOLESTEROLEMIA

The invention is concerned with novel steroids of the formula

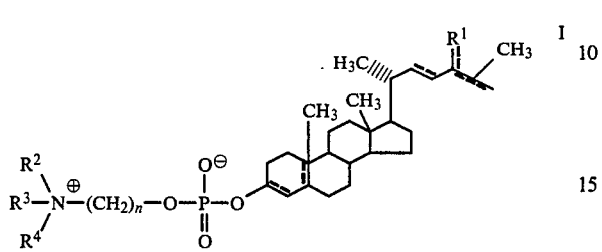

wherein n is 2,3 or 4; $R^1$ is hydrogen, lower-alkyl or lower-alkylidene; $R^2$, $R^3$ and $R^4$ are hydrogen or lower-alkyl and the dotted C—C bonds in the 5(6)-, 7(8)-, 22(23)-, 24(28)- and 25(26)-positions are optional, with the provisos that the B-ring contains only one double bond and the side-chain is either saturated, mono-unsaturated, or di-unsaturated in the 22(23) and 25(26)-positions; and with the further proviso that $R^1$ is lower-alkyl or lower-alkylidene when a 5(6)-double bond is present, n is the number 2 and $R^2$, $R^3$ and $R^4$ are methyl, and pharmaceutically acceptable salts of these steroids.

The steroids in accordance with the invention are distinguished by valuable pharmacological properties and can be used in the control or prevention of illnesses.

The invention is furthermore concerned with a process for the manufacture of these steroids, medicaments based on these steroids, and these steroids as pharmaceutically active substances, especially in the inhibition of the intestinal resorption of cholesterol.

The term "lower" signifies that the residues denoted thereby contain up to 4 carbon atoms and can be straight-chain or branched. Methyl, ethyl, n-propyl, isopropyl, n-butyl and t-butyl are examples of lower-alkyl residues.

Pharmaceutically acceptable salts of the steroids of formula I are inorganic salts such as hydrochlorides and sulphates; organic salts such as trifluoroacetates, mesylates and tosylates; and metal salts such as sodium salts. The compounds of formula I in which at least one of the residues $R^2$, $R^3$ and $R^4$ is hydrogen can be present in the form of a zwitterion or a hydrogen phosphate.

Among the steroids of formula I there are preferred those in which $R^1$ is hydrogen or lower-alkyl, especially ethyl, further those in which $R^2$, $R^3$ and $R^4$ are lower-alkyl, especially methyl, as well as those in which n is the number 2. The saturated steroids of formula I as well as the 5(6)- and 22(23)-di-unsaturated steroids are also preferred. 3β-Stigmastanyloxy-phosphorylcholine and stigmasta-5,22-dien-3β-yloxy-phosphorylcholine are especially preferred.

The steroids of formula I and the salts thereof can be manufactured by (a) reacting a compound of the formula

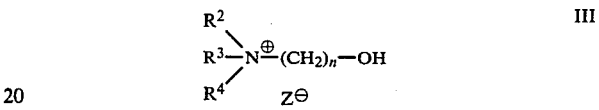

with a salt of the formula

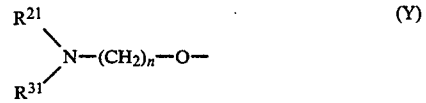

wherein n, $R^1$, $R^2$, $R^3$, $R^4$ and the dotted C—C bonds have the significances given above; X and Y are chlorine, bromine or iodine or X and Y together are the 1,2-dimethylethylenedioxy residue and Z is lower-alkylsulphonyloxy, arylsulphonyloxy, perchloryloxy, chloro, bromo or iodo,
in the presence of a base and hydrolyzing the reaction product, or (b) reacting a compound of formula II in which X is a metallized hydroxy group and Y is a group of the formula Hal—$(CH_2)_n$—O—, wherein Hal is chlorine, bromine or iodine and n has the above significance, or in which X and Y to-gether form the ethylenedioxy residue with an amine of the formula $N(R^2,R^3,R^4)$, wherein $R^2$, $R^3$ and $R^4$ have the above significance, or (c) cleaving off the amino protecting group in a compound of formula II in which X is a metallized hydroxy group and Y is a residue of the formula $$\begin{array}{c} R^{21} \\ \phantom{R^{21}}\diagdown \\ \phantom{R^{21}\diagdown}N-(CH_2)_n-O- \\ \phantom{R^{21}}\diagup \\ R^{31} \end{array} \quad (Y)$$

wherein one of $R^{21}$ and $R^{31}$ is an amino protecting group and the other has the significance of $R^2$ or $R^{21}$ and $R^{31}$ together with the N-atom are a protected amino group and n and $R^2$ have the above significance, and (d) isolating a steroid of formula I obtained in this form or in the form of a salt.

For the manufacture of the products in accordance with the invention the starting material of formula II is conveniently prepared in the manner described below from a corresponding steroid of formula IV shortly or immediately before the reaction with a compound of formula III or an amine of the formula $N(R^2,R^3,R^4)$ or before the cleavage of the amino protecting group and is introduced into the re-action as the crude product.

In process variant (a) steroids of formula II in which X and Y are chlorine are preferably reacted with salts of formula III in which Z is lower-alkylsulphonyloxy or arylsulphonyloxy, especially with mesylates or tosylates. Organic bases such as tri-(lower-alkyl)-amines, e.g. trimethylamine or triethylamine; quinoline or pyridine; or inorganic bases such as alkali metal or alkaline earth metal hydroxides, carbonates or bicarbonates such as $Na_2CO_3$, $KHCO_3$ or $Ca_2CO_3$ can be used as bases. The reaction can be carried out in a solvent such as a halogenated hydrocarbon, e.g. chloroform, methylene chloride or di-chloroethylene; or acetonitrile or in a mixture thereof.

The subsequent hydrolysis can be carried out with water or with a dilute acid such as hydrochloric acid or a base such as one of the organic or inorganic bases mentioned above.

The temperature is not critical in process variant (a). However, it is preferably carried out at room temperature.

In process variant (b) there are conveniently used steroids of formula II in which X is a hydroxy group metallized with an alkali metal or alkaline earth metal, preferably a group —ONa, and Y is a group of the formula $Hal—(CH_2)_n—O—$, preferably of the formula $Cl—(CH_2)_n—O—$. The reaction of such a steroid II with an amine $N(R^2,R^3,R^4)$ is conveniently carried out in a solvent such as a halogenated hydrocarbon, e.g. chloroform, an alcohol, e.g. ethanol or 2-propanol; in acetonitrile or DMF, or in a mixture thereof. The temperature is not critical. However, it is preferably carried out at room temperature.

In process variant (b) a steroid of formula II in which X and Y together form an ethylenedioxy group can also be reacted with an amine $N(R^2,R^3,R^4)$. The reaction is conveniently carried out under pressure and while heating, preferably under 1 to 20 atm at a temperature between 20° and 100° C., whereby one of the solvents quoted for process variant (a) can be used.

In process variant (c) there is conveniently reacted a steroid of formula II in which X is a hydroxy group metallized with an alkali metal, preferably sodium. Examples of amino protecting groups $R^{21}$ or $R^{31}$ present in the residue Y are benzyloxycarbonyl, phenoxycarbonyl, formyl, trifluoromethylcarbonyl, trimethylsilyl and trityl. Examples of protected amino groups $—N(R^{21},R^{31})$ are succinimide and phthalimide groups. Such amino protecting groups can be cleaved off in a manner known per se, e.g. a benzyloxycarbonyl group by hydrogenolysis or by means of hydrobromic acid and acetic acid, the trityl group by means of hydrobromic acid and acetic acid, and the phthalimide group with hydrazine hydrate in an alcohol such as methanol.

The steroids of formula II used as starting materials can be prepared, as already mentioned above, from corresponding steroids of the formula

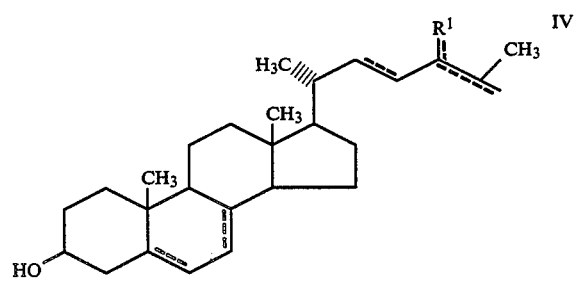

wherein $R^1$ and the dotted C—C bonds have the above significance.

The steroids of formula II used in process variant (a) can be prepared by reacting a steroid of formula IV with a compound of the formula $PO(Hal)_3$ or $(Hal)_2POOPO(Hal)_2$ or

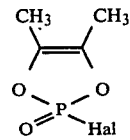

wherein Hal is chlorine, bromine or iodine, in the presence of a base, optionally in a solvent. A compound of the formula $PO(Hal)_3$, preferably $POCl_3$, or 1,2-dimethylethylenedioxy-phosphoryl chloride is conveniently used. As the base and the solvent there can be used the same as used for process variant (a).

The steroids of formula II in which X is a metallized hydroxy group and Y is a group of the formula $Hal—(CH_2)_n—O—$ which are used in process variant (b) can be prepared by reacting a steroid of formula IV with a compound of the formula

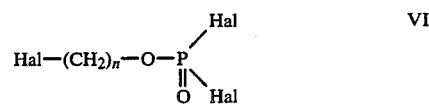

wherein Hal and n have the above significance, in the presence of a base in a solvent and hydrolyzing the reaction product with a dilute inorganic base in a solvent. As the base and the solvent for the reaction of the compounds of formulae IV and VI or as the inorganic base for the subsequent hydrolysis there can be used the same as used for process variant (a). An ether such as THF or dioxan or a ketone such as acetone is used as the solvent for the hydrolysis.

The steroids of formula II in which X and Y together form an ethylenedioxy residue which are used in process variant (b) can be prepared by reacting a steroid of formula IV with a compound of the formula

wherein Hal has the above significance, e.g. with 2-chloro-2-oxo-1,3,2-dioxaphospholane, in the presence of a base, optionally in a solvent. As the base and the solvent there can be used the same as used for process variant (a).

The steroids of formula II used in process variant (c) can be prepared by reacting a steroid of formula IV with a compound of the formula

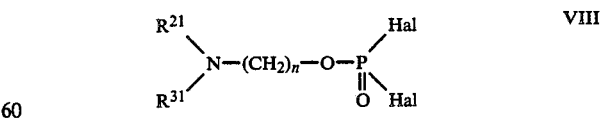

wherein $R^{21}$, $R^{31}$, Hal and n have the above significance, in the presence of a base, optionally in a solvent. As the base and the solvent there can be used the same as used for process variant (a).

The steroids of formula I inhibit the intestinal resorption of cholesterol.

The inhibition of the intestinal resorption of cholesterol can be demonstrated as follows in an animal experiment:

Squirrel monkeys are orally administered the substances to be investigated together with a feed containing a protein, starch, triolein and [26-$^{14}$C]-cholesterol. Thereupon, the faeces is collected for 2.5 days. The difference between the administered and the excreted radioactive cholesterol determined in the faeces is taken as the measurement of resorbed cholesterol. The cholesterol resorption (CHORES) is expressed in percentages of the control values determined prior to the medication.

The results which have been obtained with some representative products in accordance with the invention are reproduced in the Table hereinafter. There are given for each of the compounds indicated therein the dosage administered (in μmol/kg p.o.) as well as in each case the cholesterol resorption (CHORES) determined in percentages of the cholesterol resorption in the pre-period. Moreover, the Table contains data concerning the acute toxicity of the compounds investigated (LD$_{50}$ in mg/kg in the case of single oral administration to mice).

TABLE

| Compound of formula I | Dosage in μmol/kg p.o. | CHORES in % of the pre-period | LD$_{50}$ in mg/kg p.o. |
|---|---|---|---|
| 3β-Cholestanyloxy-phosphorylcholine | 100 | 26 | 5000 |
| Stigmast-5-en-3β-yloxy-phosphorylcholine | 100 | 52 | 5000 |
| Stigmasta-5,22-dien-3β-yloxy-phosphorylcholine | 100 | 33 | 5000 |
| 3β-Stigmastanyloxy-phosphorylcholine | 100 | 36 | 4000 |

The products in accordance with the invention can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions.

For the manufacture of pharmaceutical preparations the products in accordance with the invention can be administered with pharmaceutically inert, inorganic or organic carriers. Lactose, maize starch or derivatives thereof, talc, stearic acid or its salts and the like can be used, for example, as such carriers for tablets, coated tablets, dragées and hard gelatine capsules. Vegetable oils, waxes, fats, semi-solid and liquid polyols and the like are, for example, suitable as carriers for soft gelatine capsules; depending on the nature of the active substance no carrier is, however, generally required in the case of soft gelatine capsules. Water, polyols, saccarose, invert sugar, glucose and the like are, for example, suitable as carriers for the manufacture of solutions and syrups.

The pharmaceutical preparations can, moreover, contain preserving agents, solubilizers, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, medicaments containing a steroid of formula I or a pharmaceutically acceptable salt thereof are also an object of the present invention, as is a process for the manufacture of such medicaments, which process comprises bringing one or more products in accordance with the invention and, if desired, one or more other therapeutically valuable substances into a galenical administration form. As mentioned earlier, the products in accordance with the invention can be used in the control or prevention of illnesses.

They can be used especially in the control or prevention of hypercholesterolaemia and of atherosclerosis. The dosage can vary within wide limits and is, of course, fitted to the individual requirements in each particular case. In general, in the case of oral administration a daily dosage of about 50 mg to about 3 g, preferably of about 200 mg to about 1 g, should be appropriate.

The following Examples are intended to illustrate the present invention in more detail, but are not intended to limit its extent in any manner. All temperatures are given in degrees Celsius.

EXAMPLE 1

A solution of 7.78 g (16.7 mmol) of β-sitosterol and 2.5 ml (20.8 mmol) of quinoline in 100 ml of chloroform is added dropwise at room temperature to a solution of 1.95 ml (20.8 mmol) of phosphorus oxychloride. The solution is then heated to 45° and then treated at room temperature with 10 g (36.3 mmol) of choline tosylate and 10 ml of pyridine, whereupon the reaction mixture is stirred at room temperature. The mixture is treated with 3 ml of water. The mixture is dissolved in 150 ml of chloroform and washed successively with in each case 2×50 ml of water, 3% sodium carbonate solution, water, 5% HCl solution and water. The organic phase is dried and evaporated. The residue is chromatographed on silica gel while eluting with chloroform-methanol-water (40:55:5). The product is treated with toluene by azeotropic distillation and then recrystallized in chloroform-ether. Stigmast-5-en-3β-yloxy-phosphorylcholine of melting point 285°–286° is obtained.

EXAMPLE 2

Stigmasta-5,22-dien-3β-yloxy-phosphorylcholine of melting point 228° (decomposition) is manufactured in a manner analogous to Example 1.

EXAMPLE 3

3β-Cholestanyloxy-phosphorylcholine of melting point 281°–283° is manufactured in a manner analogous to Example 1.

EXAMPLE 4

A. Preparation of the Starting Material (a) A solution of 17 g (70.4 mmol) of 2-bromoethyl-phosphoric acid dichloride in 90 ml of trichloroethylene is cooled to 0°–5° and treated with 14.26 g (141 mmol) of triethylamine. A solution of 16.28 g (39.07 mmol) of stigmastanol in 100 ml of trichloroethylene is added dropwise under argon while stirring at 25°, whereupon the temperature of the solution is held between 25°–30°. The solution is then stirred at 25° and treated with 180 ml of toluene. The precipitated triethylamine chlorohydrate is filtered off under suction. The filtrate is dried at 50° under reduced pressure. (2-Bromoethyl)-(3β-stigmastanyl)-phosphorchloridate is obtained in the form of an oily residue.

(b) This residue is dissolved in 160 ml of tetrahydrofuran and treated with 350 ml of 0.5M sodium acetate. The solution obtained (pH 4.5) is stirred. 17.6 ml of 0.5M EDTA are added thereto and the pH of the solution is brought to 9.5 by the addition of 45 ml of 3N NaOH. The reaction mixture is extracted with 350 ml of diisopropyl ether and 140 ml of MeOH. The organic phase is evaporated. The residue is recrystallized from chloroform-methanol-acetone, the crystals obtained are washed with acetone and ether and dried at 45°. Sodium (2-bromoethyl)-(3β-stigmastanyl)-phosphate is obtained in the form of white crystals.

For analysis, 500 mg of these crystals are acidified with 2N HCl and extracted with ether. The residue is recrystallized in ether-n-hexane. (2-Bromoethyl)-(3β-stigmastanyl)-hydrogen phosphate of melting point 129°–130° is obtained.

B. Manufacture of the Product

A solution of 5 g (8 mmol) of sodium (2-bromoethyl)-(3β-stigmastanyl)-phosphate in 25 ml of chloroform, 40 ml of 2-propanol and 40 ml of acetonitrile is treated with 60 ml of 45% aqueous trimethylamine, stirred at room temperature and then evaporated. The residue is taken up in 125 ml of water and extracted with 250 ml of chloroform-methanol (1:1). The organic phase is dried and evaporated. By chromatography on silica gel while eluting with $CHCl_3$—MeOH (8:2 to 6:4) and then with $CHCl_3$—MeOH—$H_2O$ (60:35:5) and recrystallization from chloroform-ether there is obtained 3β-stigmastanyloxy-phosphorylcholine of melting point 270° (decomposition).

EXAMPLE 5

(2-Dimethylaminoethyl)-(3β-stigmastanyl)-hydrogen phosphate of melting point 267° (decomposition) is obtained in a manner analogous to Example 4B using dimethylamine in place of trimethylamine.

EXAMPLE 6

(2-Methylaminoethyl)-(3β-stigmastanyl)-hydrogen phosphate of melting point 258°–260° (decomposition) is obtained in a manner analogous to Example 4B using methylamine in place of trimethylamine.

EXAMPLE 7

A solution of 5 g (8 mmol) of sodium (2-bromoethyl)-(3β-stigmastanyl)-phosphate in 80 ml of chloroform, 80 ml of 2-propanol and 320 ml of dimethylformamide is treated with 240 ml of 25% ammonia, stirred at room temperature and then concentrated. The aqueous DMF phase is acidified with 2N hydrochloric acid and extracted with 1.5 l of $CHCl_3$—MeOH (50:50). The organic phase is dried and evaporated. By chromatography on silica gel while eluting with chloroform-methanol (7:3) and chloroform-methanol-water (60:35:5) there is obtained (2-aminoethyl)-(3β-stigmastanyl)-phosphate hydrochloride of melting point 202°.

EXAMPLE 8

In a manner analogous to Example 4, starting from stigmastanol and 3-bromopropylphosphoric acid dichloride via (3-bromopropyl)-(3β-stigmastanyl)-phosphorochloridate and sodium (3-bromopropyl)-(3β-stigmastanyl)-phosphate there is obtained 3-(3β-stigmastanyloxy-phosphoryl)propylamine of melting point 270° (decomposition).

EXAMPLE A

3β-Stigmastanyloxy-phosphorylcholine can be used as follows as the active substance for the manufacture of pharmaceutical preparations:

| (a) Tablets | 1 tablet contains |
| --- | --- |
| Active substance | 200 mg |
| Microcrystalline cellulose | 155 mg |
| Maize starch | 25 mg |
| Talc | 25 mg |
| Hydroxypropylmethylcellulose | 20 mg |
| | 425 mg |

The active substance is mixed with half of the microcrystalline cellulose and granulated with a 10 percent solution of hydroxypropylmethylcellulose in a mixture of isopropanol and methylene chloride. The granulate is dried, sieved and mixed with the remainder of the adjuvants. It is then pressed on a press to biplanar tablets of 12 mm diameter with a break-bar.

| (b) Capsules | 1 capsule contains |
| --- | --- |
| Active substance | 100 0 mg |
| Maize starch | 20.0 mg |
| Lactose | 95.0 mg |
| Talc | 4.5 mg |
| Magnesium stearate | 0.5 mg |
| | 220.0 mg |

The active substance is mixed with the adjuvants and sieved. After renewed mixing, the capsule fill mass obtained is filled into interlocking gelatine capsules of suitable size on a fully automatic capsule filling machine.

I claim:
1. Steroids of the formula

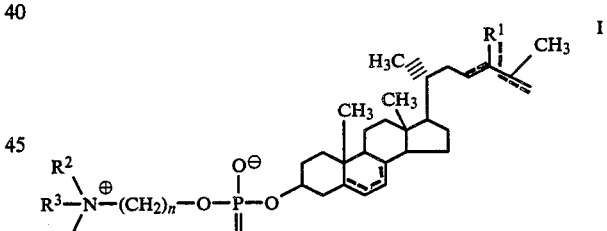

wherein n is 2,3 or 4; $R^1$ is hydrogen, or lower-alkyl; $R^2$, $R^3$ and $R^4$ are hydrogen or lower-alkyl and the dotted C—C bonds in the 5(6)-, 7(8)-, 22(23)-, and 25(26)-positions are optional, with the provisos that the B-ring contains only one double bond and the side-chain is either saturated, mono-unsaturated, or di-unsaturated in the 22(23) and 25(26)-positions; and with the further proviso that $R^1$ is lower-alkyl when a 5(6)-double bond is present, n is the number 2 and $R^2$, $R^3$ and $R^4$ are methyl,
and pharmaceutically acceptable salts of these steroids.

2. Steroids according to claim 1 wherein $R^1$ is ethyl.
3. Steroids according to claim 1 wherein $R^2$, $R^3$ and $R^4$ are lower-alkyl.
4. Steroids according to claim 3 wherein $R^2$, $R^3$ and $R^4$ are methyl.
5. Steroids according to claim 1 wherein n is 2.
6. Saturated steroids according to claim 1.

7. 5(6)- and 22(23)-di-unsaturated steroids according to claim 1.

8. Steroids according to claim 1 wherein $R^1$ is hydrogen or lower-alkyl; $R^2$, $R^3$ and $R^4$ are lower-alkyl; and, n is 2.

9. Fully saturated steroids according to claim 8.

10. 5(6)- and 22(23)-di-unsaturated steroids according to claim 8.

11. Steroids according to claim 8 wherein $R^1$ is ethyl and $R^2$, $R^3$ and $R^4$ are methyl.

12. Saturated steroids according to claim 11.

13. 5(6)- and 22(23)-di-unsaturated steroids according to claim 11.

14. In accordance with claim 12, the compound 3β-Stigmastanyloxy-phosphorylcholine.

15. In accordance with claim 13, the compound Stigmasta-5,22-dien-3β-yloxy-phosphorylcholine.

16. A method for treatment of hypercholesterolaemia which comprises administering to a host requiring such treatment a pharmaceutically effective amount of a steroid of the formula

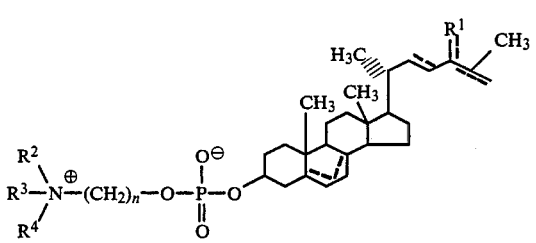

wherein n is 2, 3 or 4; $R^1$ is hydrogen, or lower-alkyl; $R^2$, $R^3$ and $R^4$ are hydrogen or lower-alkyl and the dotted C—C bonds in the 5(6)-, 7(8)-, 22(23)-, and 25(26)-positions are optional, with the provisos that the B-ring contains only one double bond and the side-chain is either saturated, mono-unsaturated, or di-unsaturated in the 22(23) and 25(26)-positions; and with the further proviso that $R^1$ is lower-alkyl when a 5(6)-double bond is present, n is the number 2 and $R^2$, $R^3$ and $R^4$ are methyl, or a pharmaceutically acceptable salt thereof.

17. A process for the manufacture of a steroid of the formula

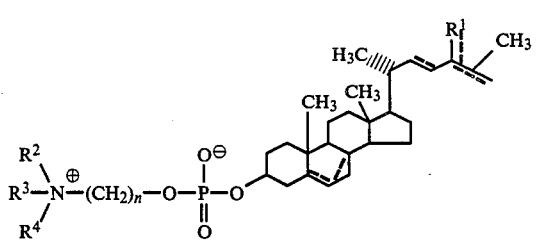

wherein n is 2,3 or 4; $R^1$ is hydrogen, or lower-alkyl; $R^2$, $R^3$ and $R^4$ are hydrogen or lower-alkyl and the dotted C—C bonds in the 5(6)-, 7(8)-, 22(23)-, and 25(26)-positions are optional, with the provisos that the B-ring contains only one double bond and the side-chain is either saturated, mono-unsaturated, or di-unsaturated in the 22(23) and 25(26)-positions; and with the further proviso that $R^1$ is lower-alkyl when a 5(6)-double bond is present, n is the number 2 and $R^2$, $R^3$ and $R^4$ are methyl, or a pharmaceutically acceptable salt thereof, which process comprises reacting a compound of the formula

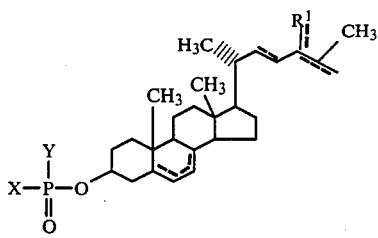

with a salt of the formula

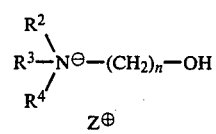

wherein n, $R^1$, $R^2$, $R^3$, $R^4$ and the dotted C—C bonds are as hereinbefore defined; X and Y are chlorine, bromine or iodine or X and Y together are a 1,2-dimethylethylenedioxy residue and Z is lower-alkylsulphonyloxy, arylsulphonyloxy, perchloryloxy, chloro, bromo or iodo, in the presence of a base and hydrolyzing the product.

18. A process for the manufacture of a steroid of the formula

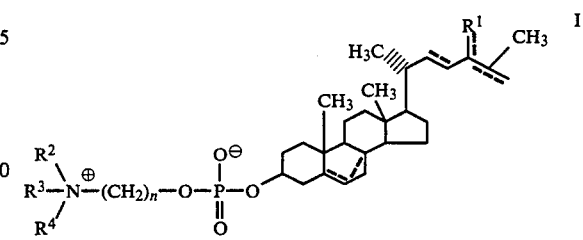

wherein n is 2, 3 or 4; $R^1$ is hydrogen, or lower-alkyl; $R^2$, $R^3$ and $R^4$ are hydrogen or lower-alkyl and the dotted C—C bonds in the 5(6)-, 7(8)-, 22(23)-, and 25(26)-positions are optional, with the provisos that the B-ring contains only one double bond and the side-chain is either saturated, mono-unsaturated, or di-unsaturated in the 22(23) and 25(26)-positions; and with the further proviso that $R^1$ is lower-alkyl when a 5(6)-double bond is present, n is the number 2 and $R^2$, $R^3$ and $R^4$ are methyl, or a pharmaceutically acceptable salt thereof, which process comprises reacting a compound of the formula

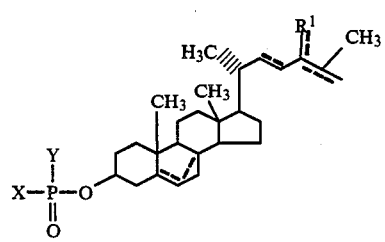

wherein X is a metallized hydroxy group and Y is a group of the formula Hal—(CH$_2$)$_n$—O, wherein Hal is chlorine, bromine, or iodine and n is as hereinbefore defined, or in which X and Y together form an ethylenedioxy residue with an amine of the formula N(R$^2$,R$^3$,R$^4$) and wherein R$^1$, R$^2$, R$^3$ and R$^4$ are as hereinbefore defined.

19. A process for the manufacture of a steroid of the formula

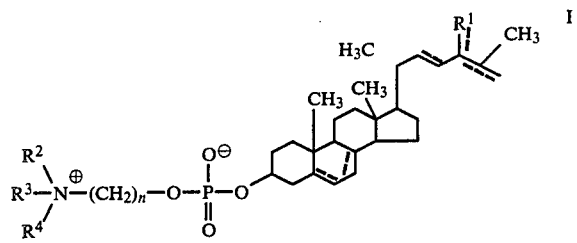

wherein n is 2, 3 or 4; R$^1$ is hydrogen, or lower-alkyl; R$^2$, R$^3$ and R$^4$ are hydrogen or lower-alkyl and the dotted C—C bonds in the 5(6)-, 7(8)-, 22(23)-, and 25(26)-positions are optional, with the provisos that the B-ring contains only one double bond and the side-chain is either saturated, mono-unsaturated, or di-unsaturated in the 22(23) and 25(26)-positions; and with the further proviso that R$^1$ is lower-alkyl when a 5(6)-double bond is present, n is the number 2 and R$^2$, R$^3$ and R$^4$ are methyl, or a pharmaceutically acceptable salt thereof, which process comprises cleaving off the amino protecting group in a compound of the formula

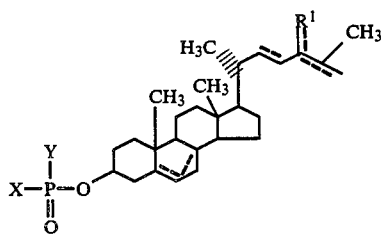

in which X is a metallized hydroxy group and Y is residue of the formula

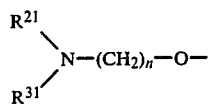

wherein one of R$^{21}$ and R$^{31}$ is an amino protecting group and the other is the same as R$^2$, or R$^{21}$ and R$^{31}$ together with the N-atom are a protected amino group, and n and R$^2$ are as hereinbefore defined.

20. A composition comprising a therapeutically effective amount of a steroid of the formula

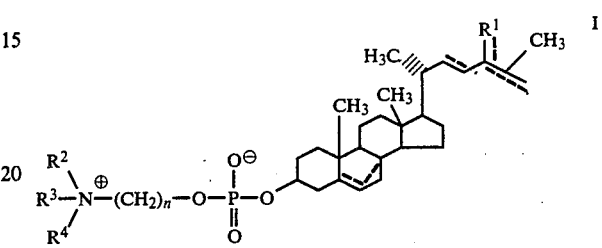

wherein n is 2, 3 or 4; R$^1$ is hydrogen, or lower-alkyl; R$^2$, R$^3$ and R$^4$ are hydrogen or lower-alkyl and the dotted C—C bonds in the 5(6)-, 7(8)-, 22(23)-, and 25(26)-positions are optional, with the provisos that the B-ring contains only one double bond and the side-chain is either saturated, mono-unsaturated, or di-unsaturated in the 22(23) and 25(26)-positions; and with the further proviso that R$^1$ is lower-alkyl when a 5(6)-double bond is present, n is the number 2 and R$^2$, R$^3$ and R$^4$ are methyl, or a pharmaceutically acceptable salt thereof, and a pharmaceutically acceptable carrier material.

21. A composition in accordance with claim 20, wherein the 5(6)- and 22(23)-positions are unsaturated.

22. A composition in accordance with claim 21, wherein the compound of formula I is stigmasta-5,22-dien-3β-yloxy-phosphorylcholine.

23. A composition in accordance with claim 20, wherein the compound of formula I is saturated.

24. A composition in accordance with claim 23, wherein the compound of formula I is 3β-stigmastanyloxy-phosphorylcholine.

* * * * *

UNITED STATES PATENT AND TRADEMARK OFFICE
CERTIFICATE OF CORRECTION

PATENT NO. : 4,680,290
DATED : July 14, 1987
INVENTOR(S) : Jean-Marie Cassal

Page 1 of 8

It is certified that error appears in the above—identified patent and that said Letters Patent is hereby corrected as shown below:

In the ABSTRACT of the disclosure, on the cover page, please delete

"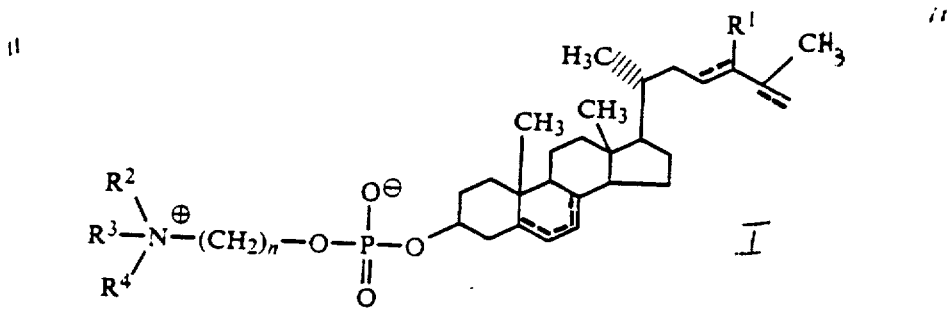"

and insert therefor

-- 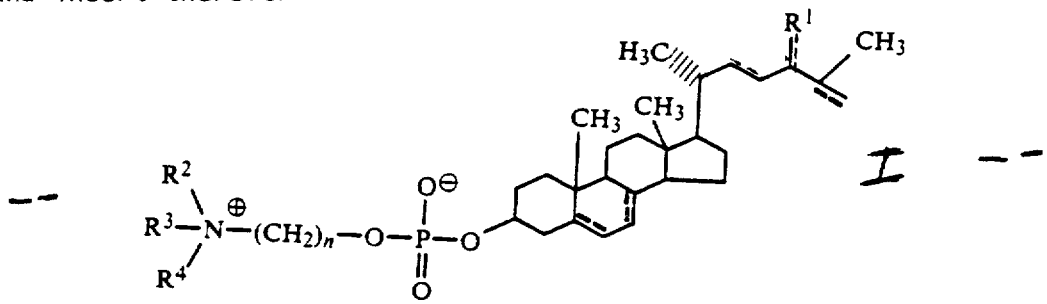 --

In column 2, lines 1-14, please delete " 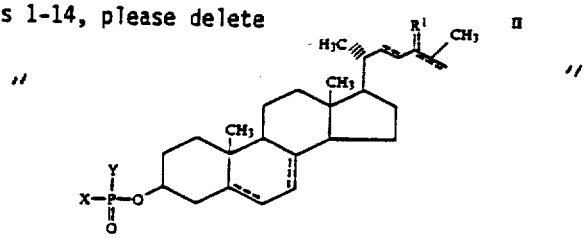 "

UNITED STATES PATENT AND TRADEMARK OFFICE
CERTIFICATE OF CORRECTION

PATENT NO. : 4,680,290
DATED : July 14, 1987
INVENTOR(S) : Jean-Marie Cassal

It is certified that error appears in the above—identified patent and that said Letters Patent is hereby corrected as shown below:

and insert therefor

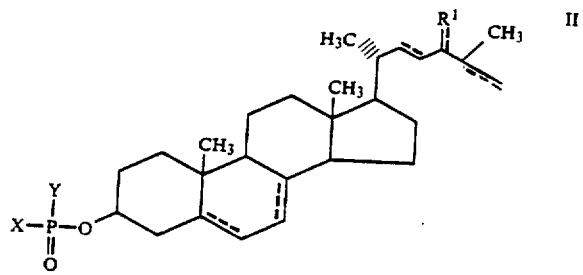

In column 3, lines 50-60, please delete

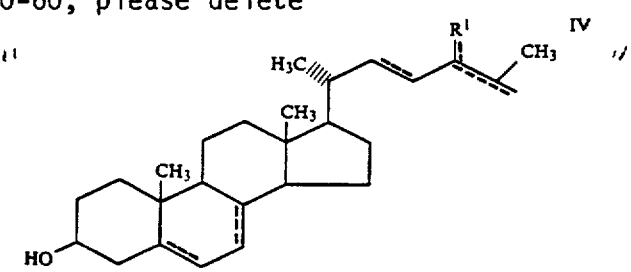

and insert therefor

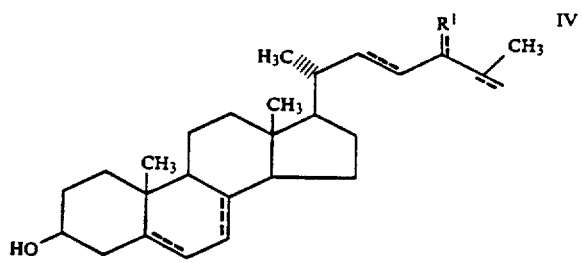

UNITED STATES PATENT AND TRADEMARK OFFICE
CERTIFICATE OF CORRECTION

PATENT NO. : 4,680,290
DATED : July 14, 1987
INVENTOR(S) : Jean-Marie Cassal

It is certified that error appears in the above—identified patent and that said Letters Patent is hereby corrected as shown below:

In claim 1, line 2, please delete "

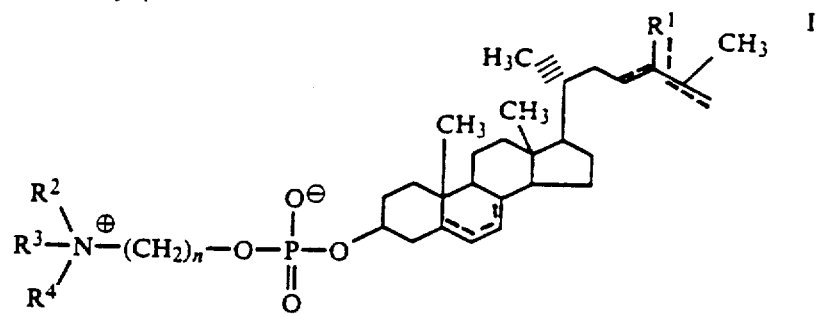

and insert therefor

-- 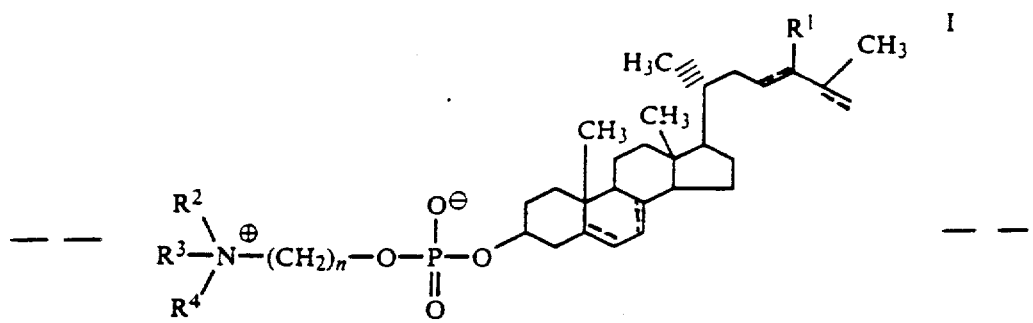 --

UNITED STATES PATENT AND TRADEMARK OFFICE
CERTIFICATE OF CORRECTION

PATENT NO. : 4,680,290
DATED : July 14, 1987
INVENTOR(S) : Jean-Marie Cassal

Page 4 of 8

It is certified that error appears in the above—identified patent and that said Letters Patent is hereby corrected as shown below:

In claim 16, line 5;
  claim 17, line 3;
  claim 18, line 3; and
  claim 20, line 3; please delete

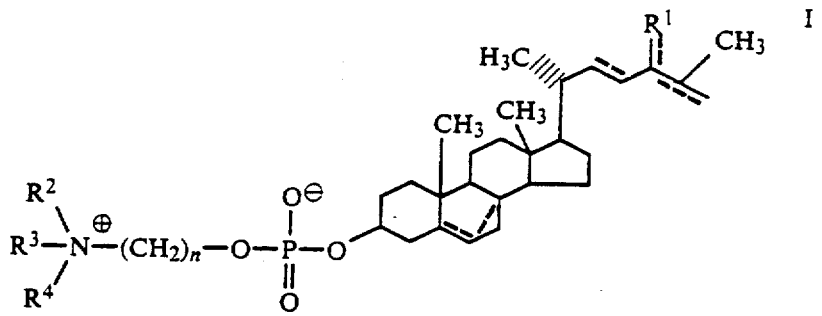

and insert therefor

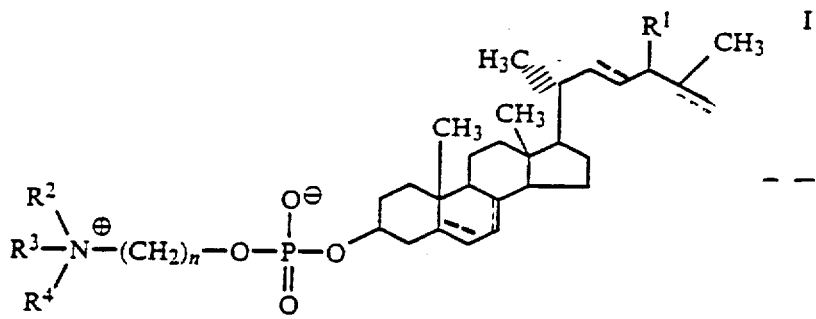

UNITED STATES PATENT AND TRADEMARK OFFICE
CERTIFICATE OF CORRECTION

PATENT NO. : 4,680,290
DATED : July 14, 1987
INVENTOR(S) : Jean-Marie Cassal

Page 5 of 8

It is certified that error appears in the above—identified patent and that said Letters Patent is hereby corrected as shown below:

In claim 17, line 16;

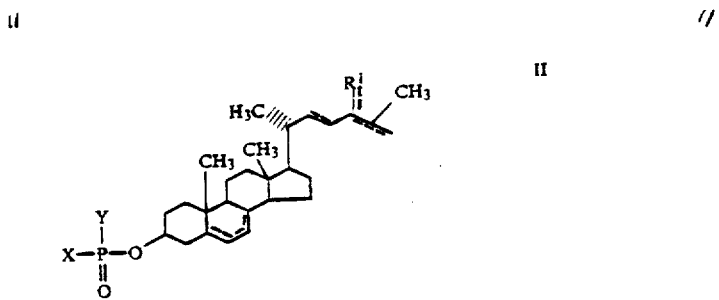

and insert therefor

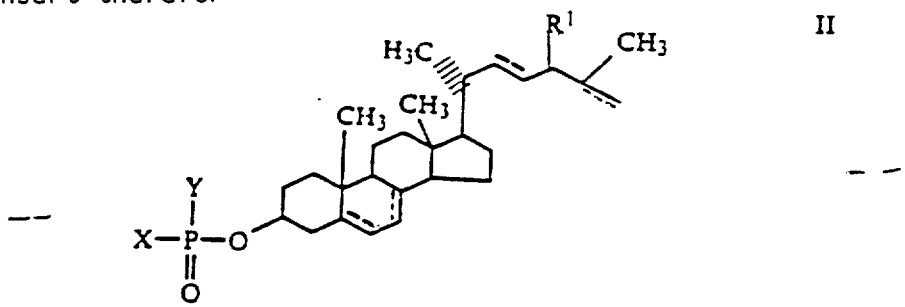

UNITED STATES PATENT AND TRADEMARK OFFICE
CERTIFICATE OF CORRECTION

PATENT NO. : 4,680,290
DATED : July 14, 1987
INVENTOR(S) : Jean-Marie Cassal

It is certified that error appears in the above—identified patent and that said Letters Patent is hereby corrected as shown below:

In claim 18, line 16 and
claim 19, line 17, please delete

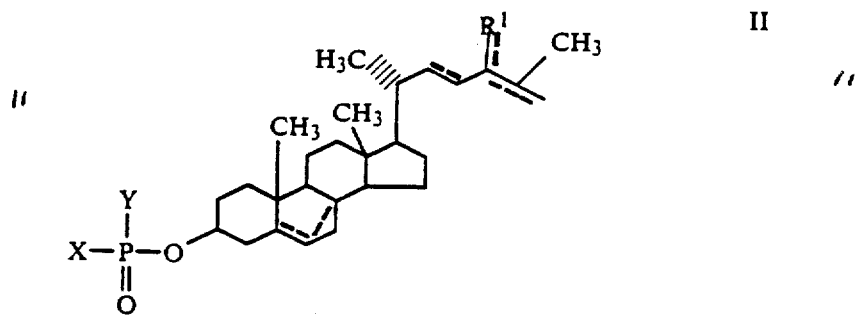

and insert therefor

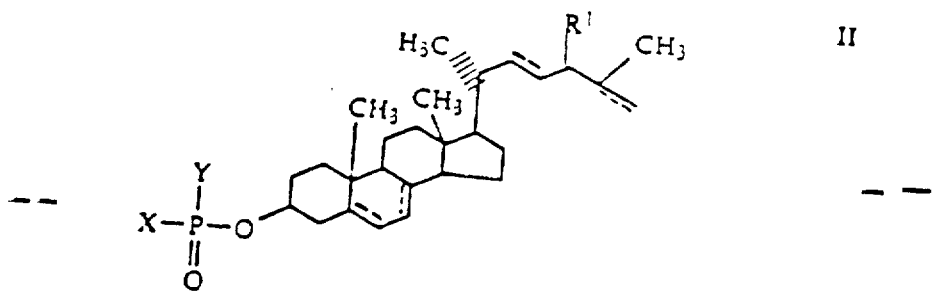

UNITED STATES PATENT AND TRADEMARK OFFICE
CERTIFICATE OF CORRECTION

PATENT NO. : 4,680,290
DATED : July 14, 1987
INVENTOR(S) : Jean-Marie Cassal

Page 7 of 8

It is certified that error appears in the above—identified patent and that said Letters Patent is hereby corrected as shown below:

In claim 19, line 3, please delete

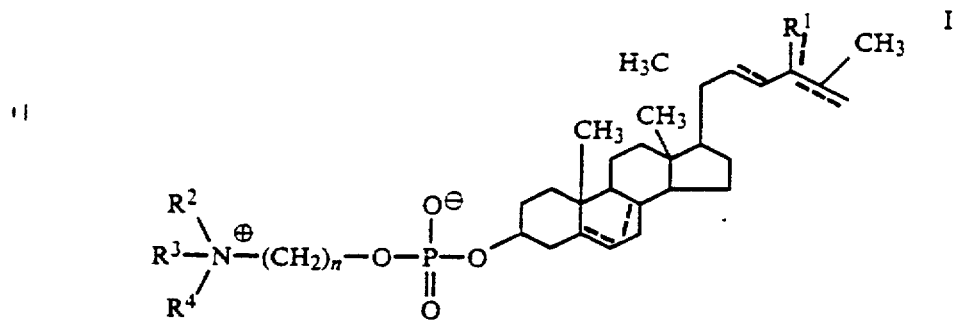

and insert therefor

UNITED STATES PATENT AND TRADEMARK OFFICE
CERTIFICATE OF CORRECTION

PATENT NO. : 4,680,290
DATED : July 14, 1987
INVENTOR(S) : Jean-Marie Cassal

Page 8 of 8

It is certified that error appears in the above-identified patent and that said Letters Patent is hereby corrected as shown below:

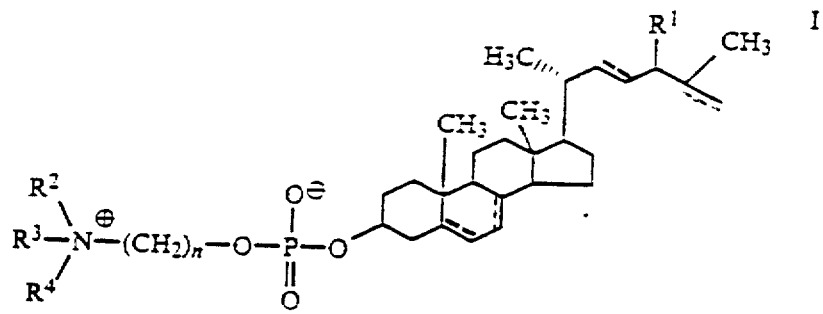

Signed and Sealed this

Tenth Day of May, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,680,290

DATED : July 14, 1987

INVENTOR(S) : Jean-Marie Cassal

It is certified that error appears in the above-identified patent and that said Letters Patent is hereby corrected as shown below:

In column 1, lines 1-18, delete

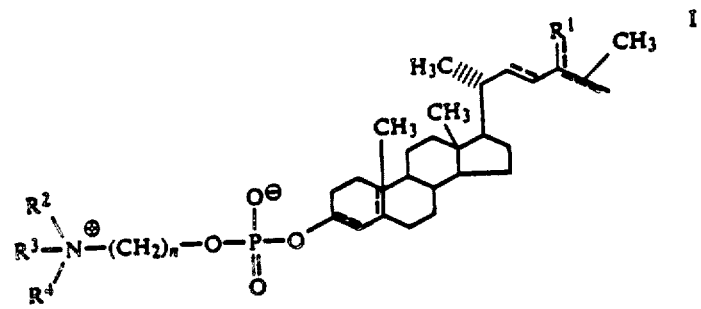

UNITED STATES PATENT AND TRADEMARK OFFICE
CERTIFICATE OF CORRECTION

PATENT NO. : 4,680,290

DATED : July 14, 1987

INVENTOR(S) : Jean-Marie Cassal

It is certified that error appears in the above-identified patent and that said Letters Patent is hereby corrected as shown below:

and insert therefor

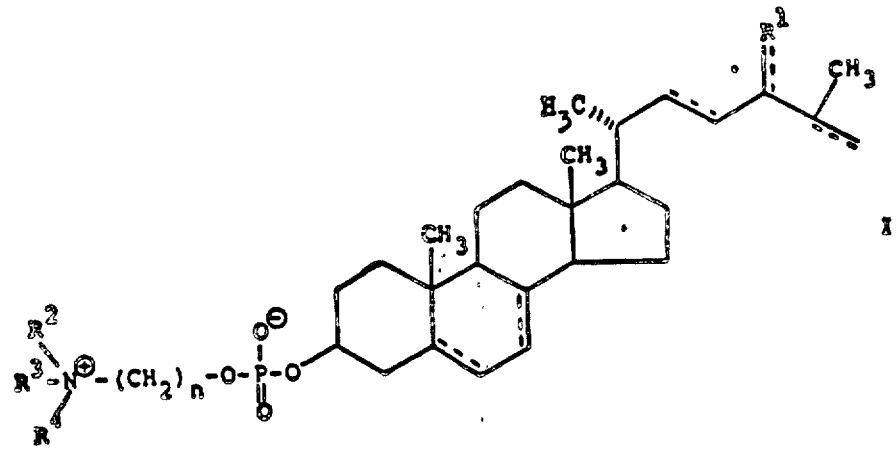

UNITED STATES PATENT AND TRADEMARK OFFICE
CERTIFICATE OF CORRECTION

PATENT NO. : 4,680,290

DATED : July 14, 1987

INVENTOR(S) : Jean-Marie Cassal

It is certified that error appears in the above-identified patent and that said Letters Patent is hereby corrected as shown below:

In claim 17, column 10, lines 20-21, delete

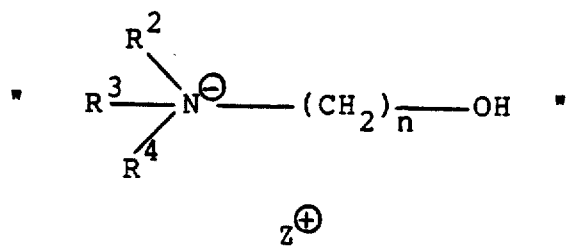

and insert therefor

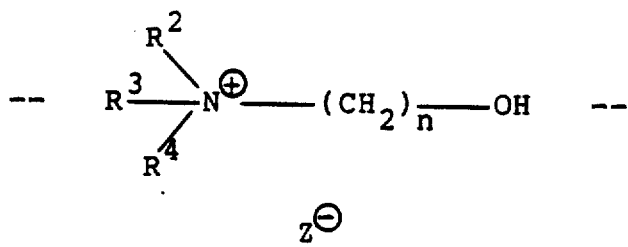

Signed and Sealed this

Sixteenth Day of August, 1988

Attest:

DONALD J. QUIGG

Attesting Officer

Commissioner of Patents and Trademarks